United States Patent [19]

Naito et al.

[11] Patent Number: 4,935,537
[45] Date of Patent: * Jun. 19, 1990

[54] PROCESS FOR PRODUCING ACYLOXYNAPHTHOIC ACIDS

[75] Inventors: Susumu Naito, Niigata; Koichi Abe, Niitsu; Hidetaka Kiga; Yuzi Onda, both of Niigata, all of Japan

[73] Assignee: Mitsubishi Gas Chemical Company, Inc., Tokyo, Japan

[*] Notice: The portion of the term of this patent subsequent to Jan. 31, 2006 has been disclaimed.

[21] Appl. No.: 263,246

[22] Filed: Oct. 27, 1988

Related U.S. Application Data

[62] Division of Ser. No. 761,520, Aug. 1, 1985, Pat. No. 4,801,737.

[30] Foreign Application Priority Data

Aug. 2, 1984 [JP] Japan .................. 59-163402
Mar. 7, 1985 [JP] Japan .................. 60-45596

[51] Int. Cl.$^5$ .................................. C07C 67/42
[52] U.S. Cl. .............................. 560/139; 260/410.5
[58] Field of Search .................. 560/139; 260/410.5

[56] References Cited

U.S. PATENT DOCUMENTS

| 3,870,754 | 3/1975 | Yamushita ............ 562/416 |
| 4,374,262 | 2/1983 | McGinnis ............ 560/56 |

FOREIGN PATENT DOCUMENTS

| 227660 | 4/1958 | Australia ............ 562/416 |
| 81753 | 6/1983 | European Pat. Off. . |
| 45-5528 | 2/1970 | Japan ............ 560/131 |
| 49-31629 | 3/1974 | Japan ............ 560/131 |

OTHER PUBLICATIONS

Sawaki, J. Am. Chem. Soc., 105, pp. 5035–5040 (1983).
Barton, "Comprehensive Organic Chemistry," vol. 1, pp. 1086–1087; vol. 2 pp. 893–896 (1979).
J. Chem. Soc. 123, pp. 1649–1657 (1923).
J. Am. Chem. Soc., 63, pp. 828–832 (1941).
J. Org. Chem., 7, pp. 374–382 (1942).
J. Am. Chem. Soc., 65, pp. 234–238 (1943).

Primary Examiner—Michael L. Shippen
Attorney, Agent, or Firm—Wenderoth, Lind & Ponack

[57] ABSTRACT

A process for producing an acyloxynaphthoic acid represented by the general formula

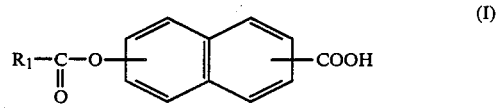

(I)

wherein $R_1$ represents a hydrogen atom or an alkyl group, which comprises
(a) oxidizing an acylalkylnaphthalene represented by the general formula

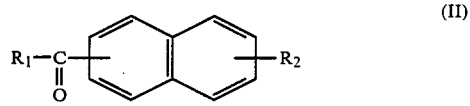

(II)

wherein $R_1$ is as defined, and $R_2$ represents a lower alkyl group, with a peroxide, and
(b) oxidizing the resulting acyloxyalkylnaphthalene represented by the general formula

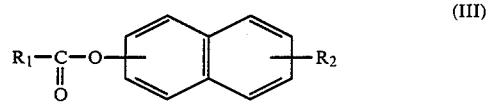

(III)

wherein $R_1$ and $R_2$ are as defined above, with molecular oxygen in an organic solvent in the presence of a catalyst comprising a bromine compound and a cobalt compound.

16 Claims, No Drawings

PROCESS FOR PRODUCING ACYLOXYNAPHTHOIC ACIDS

This application is a divisional application of application Ser. No. 761,520, filed Aug. 1, 1985, now U.S. Pat. No. 4,801,737.

This invention relates to a process for producing acyloxynaphthoic acids, and more specifically, to a new and improved process for producing acyloxynaphthoic acids represented by the formula general formula

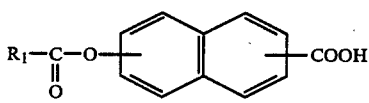

(I)

wherein $R_1$ represents a hydrogen atom or an alkyl group.

Acyloxynaphthoic acids, such as 6-acyloxy-2-naphthoic acids, have recently aroused interest as materials for producing polyesters or liquid crystal polymers, and it has been desired to develop an industrially advantageous process for producing these compounds.

The following publications disclose methods for synthesizing 6-hydroxy-2-naphthoic acid, a precursor compound of 6-acyloxy-2-naphthoic acids indicated by the following reaction schemes.

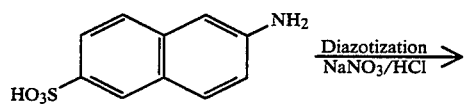

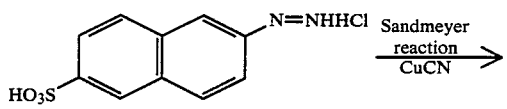

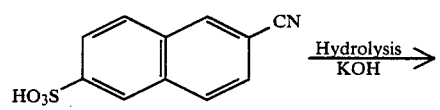

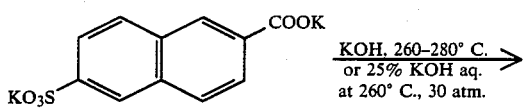

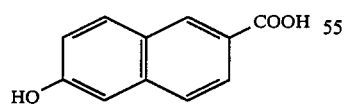

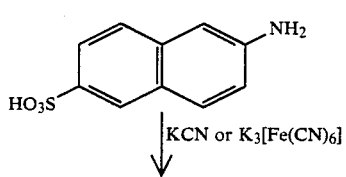

(2) Cason, J. Am. Chem. Soc., 63, 828 (1941)

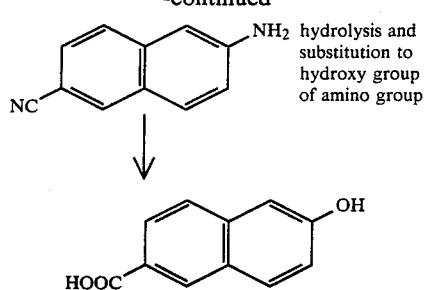

(3) Knowles et al., J. Org. Chem., 7, 374 (1942)

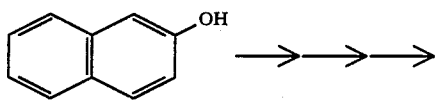

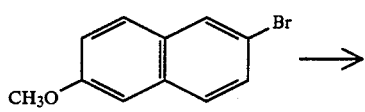

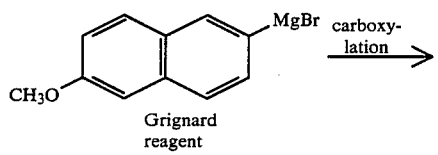

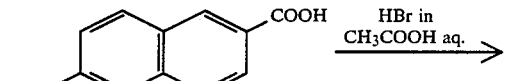

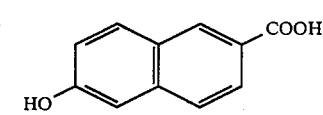

(4) Anderson et al., J. Am Chem. Soc., 65, 239 (1943)

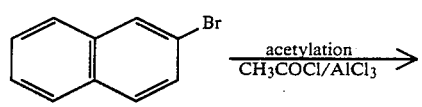

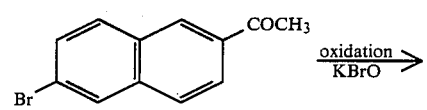

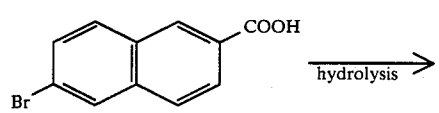

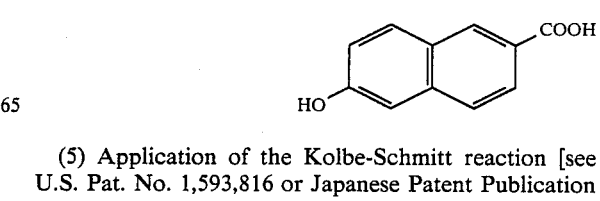

(5) Application of the Kolbe-Schmitt reaction [see U.S. Pat. No. 1,593,816 or Japanese Patent Publication No. 35911/1984 (corresponding to European Patent No. 81753)]

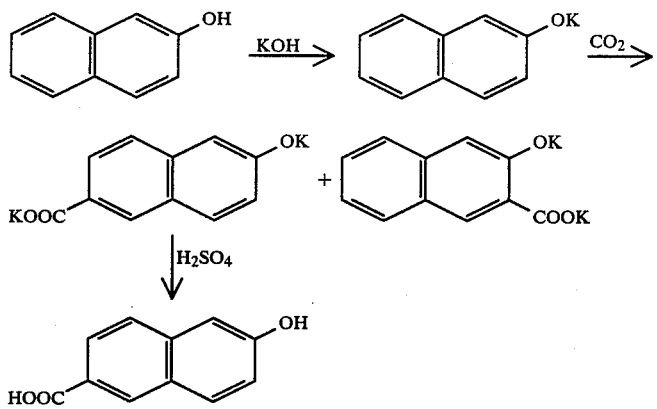

(6) Japanese Laid-Open Patent Publication No. 91955/1982 (corresponding to European Patent No. 49616 and U.S. Pat. No. 4,374,262)

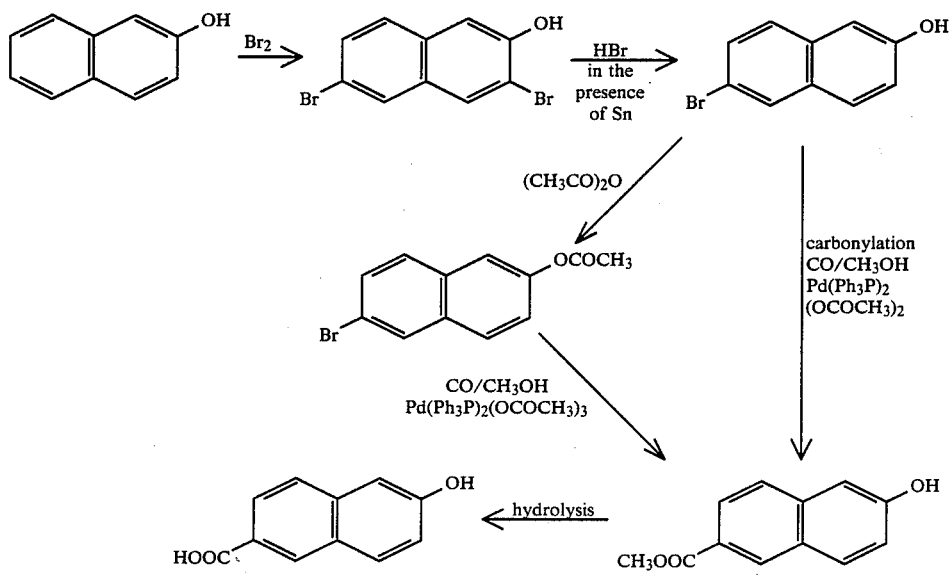

The above methods for synthesizing 6-hydroxy-2-naphthoic acid previously reported in the literature comprise relatively many steps, and require complex operations. The methods (1) and (2) are unsuitable for industrial use because they use strongly toxic hydrogen cyanide and Brönner acid which is carcinogenous. The methods (3) and (4) require the handling of reagents suspected of having carcinogenicity, such as dimethyl sulfate or nitrobenzene, and comprise many process steps. Hence, these methods are also industrially unsuitable. On the other hand, the method (5) based on the Kolbe-Schmitt reaction yield 6-hydroxy-2-naphthoic acid with a low selectivity, and the separation of by-products is time-consuming. The yield is by no means satisfactory. The method (6) also requires a special reaction or a catalyst, and the reactions involved are complex. It is not an industrially feasible method.

It is not 6-hydroxy-2-naphthoic acid itself but its acyl derivatives, 6-acyloxy-2-naphthoic acids, which are useful as materials for the production of polyesters. None of the previous methods (1) to (6) can directly give 6-acyloxy-2-naphthoic acids, and require an additional step of acylating the resutling 6-hydroxy-2-naphthoic acid.

As stated above, the previously reported methods of synthesizing hydroxynapthoic acid have some defects, and cannot be industrially advantageous.

The present inventors have worked extensively on an industrially advantageous process for producing acyloxynaphthoic acids, and have now found that by using an acylalkylnaphthalene obtained by acylation of an alkylnaphthalene as a starting material, subjecting it to two-step oxidation, namely first oxidizing it with a peroxide to form an acyloxyalkylnaphthalene, and oxidizing the resulting product with molecular oxygen, an acyloxynaphthoic acid corresponding to the starting acylalkylnaphthalene can be produced directly without going through hydroxynaphthoic acid in lesser process steps and in good yields in terms of position selection without the formation of isomers.

According to this invention, there is provided a process for producing an acyloxynaphthoic acid represented by the general formula

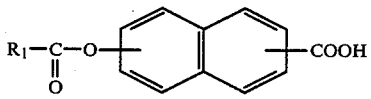

(I)

wherein $R_1$ represents a hydrogen atom or an alkyl group, which comprises (a) oxidizing an acylalkylnaphthalene represented by the general formula

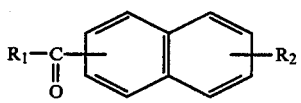

(II)

wherein $R_1$ is as defined, and $R_2$ represents a lower alkyl group, with a peroxide, and (b) oxidizing the resulting acyloxyalkylnaphthalene represented by the general formula

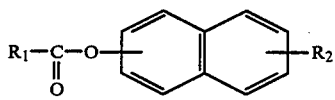

(III)

wherein $R_1$ and $R_2$ are as defined above, with molecular oxygen in an organic solvent in the presence of a catalyst comprising a bromine compound and a cobalt compound.

The term "lower", as used in the present specification and the appended claims, means that a group or compound qualified by this term has not more than 5, preferably not more than 4, carbon atoms.

In the above formulae, the "alkyl group" is a linear or branched saturated aliphatic hydrocarbon group, such as methyl, ethyl, propyl, isopropyl, butyl, isobutyl, sec-butyl, tert-butyl, pentyl, neopentyl, hexyl, heptyl, octyl, 2-ethylhexyl, nonyl, and decyl. The "alkyl group" defined for $R_1$ is preferably an alkyl group having 1 to 10 carbon atoms, especially a lower alkyl group. On the other hand, the "lower alkyl group" defined for $R_2$ is preferably an alkyl group having 1 to 3 carbon atoms, above all a methyl group.

In formula (II), the position of substitution of the group

is the 6- or 7-position of the naphthalene ring, and group $R_2$ is advantageously bonded to the 1- or 2-position of the naphthalene ring.

The process of this invention will be described in detail below.

Step (a)

This step is the oxidation of the acylalkylnaphthalene of formula (II) with a peroxide. The oxidation reaction in this step itself is known as the "Baeyer-Villiger reaction", but no example of application of this reaction to acylalkylnaphthalenes has been known.

This oxidation is carried out generally in a suitable reaction medium. Organic solvents selected from the group consisting of lower aliphatic carboxylic acids and esters thereof, aromatic hydrocarbons and mixtures of two or more of these compounds are particularly advantageous as the reaction medium. Specific examples of the organic solvents are formic acid, acetic acid and propionic acid; methyl formate, ethyl formate, methyl acetate, ethyl acetate, methyl propionate and ethyl propionate; benzene, toluene, xylene and ethylbenzene; and mixtures of two or more of these. Conveniently, a mixture of a lower aliphatic carboxylic acid with a lower aliphatic carboxylic acid ester or an aromatic hydrocarbon is used. The mixing ratio of the former to the latter is not critical, but usually the suitable mixing ratio is from 95-5/5-95, preferably 95-30/5-70.

The reaction medium permissibly contains a small amount of water. Generally, it may contain water in an amount of up to 20% by weight, preferably up to 15% by weight, based on the total weight of the reaction medium. However, the use of formic acid as a part or the whole of the reaction medium is an exception. It has been found in accordance with this invention that when in this case water is caused to be present in a specified concentration in the reaction medium, the acyloxyalkylnaphthalene of formula (III) is formed in a higher yield, and the resulting acyloxyalkylnaphthalene has a high purity and without purification can be submitted to the oxidation of step (b).

Thus, according to one preferred aspect of step (a) in this invention, there is provided a process for producing an acyloxyalkylnaphthalene represented by the general formula

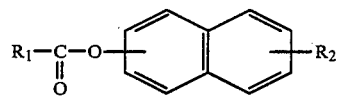

(III)

wherein $R_1$ and $R_2$ are as defined above, which comprises oxidizing an acylalkylnaphthalene represented by the general formula

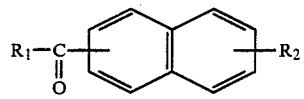

(II)

wherein $R_1$ and $R_2$ are as defined hereinabove, with a peroxide in a reaction medium composed of 45 to 95% by weight of formic acid and at least 5% by weight of water.

The preferred concentration of formic acid in the reaction midium is 55 to 95% by weight, and water is preferably present in a concentration of 5 to 45% by weight. In industrial practice, formic acid and water are conveniently prevent in concentrations near the azeotropic proportions of formic acid and water. Usually, the concentration of formic acid is 60 to 80% by weight and the concentration of water is 20 to 40% by weight.

In the preferred embodiment, formic acid and water function as a solvent, and the use of another solvent is not always necessary. If desired, however, another solvent which does not adversely afffect the present reaction may be used in combination. Examples of the other solvent are lower aliphatic carboxylic acids having at least 2 carbon atoms such as acetic acid and propionic acid; lower aliphatic carboxylic acid esters such as methyl formate, ethyl formate, methyl acetate, ethyl acetate, methyl propionate and ethyl propionate; and aromatic hydrocarbons such as benzene, toluene, xylene and ethylbenzene.

The amount of formic acid in the reaction medium may be varied depending upon the reaction conditions or the type of the starting acylalkylnaphthalene. Generally, the suitable amount of formic acid is 0.1 to 100 parts by weight, preferably 0.3 to 30 parts by weight, per part by weight of the acylalkylnaphthalene of formula (II).

The total amount of the reaction medium is not critical in particular, and can be varied widely depending upon the reaction conditions or the type of the starting compound. Amounts more than necessasry do not produce a corresponding economical effect. Hence, the amount of the reaction medium is generally 1 to 200 parts by weight, preferably 1 to 60 parts by weight, per part by weight of the starting acylalkylnaphthalene.

The oxidation of the acylalkylnaphthalene of formula (II) is carried out by using a peroxide. Hydrogen peroxide or organic peracids such as peroxyformic acid, peroxyacetic acid, peroxypropionic acid, peroxybenzoic acid, and peroxytoluic acid, or mixtures of these can be used as the peroxide. Industrially, hydrogen peroxide is preferred. Hydrogen peroxide can be fed to the reaction system as an aqueous solution having a concentration of 30 to 90% by weight. Water in the aqueous solution may form a part of the reaction medium.

The amount of the peroxide used is not strictly restricted. Usually, it is advantageous to use 0.1 to 10 moles, preferably 0.5 to 2 moles, per mole of the acylalkylnaphthalene of formula (II).

The reaction temperature is not critical, and can be varied depending upon the type of the starting compound or the peroxide, and the other reaction conditions. Generally, it may be within the range of about 0° to about 150° C., preferably about 5° to about 100° C. In the case of the aforesaid preferred embodiment, the reaction is particularly easy, and reaction temperatures of about 10° to about 70° C., preferably about 10° to about 60° C., can be used.

The acylalkylnaphthalene of formula (II) used as a starting material in the above reaction is a known compound, and can be easily produced, for example, by acylating an alkylnaphthalene represented by the following formula

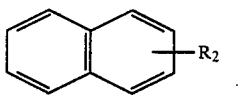 (IV)

wherein $R_2$ is as defined hereinabove, with an acylating agent of the formula $R_1COX$ wherein X is a halogen atom such as F and Cl and $R_1$ is a hydrogen atom or an alkyl group in the presence of a catalyst such as $AlCl_3$ or $BF_3$ [for example, for the acylation reaction, see J. Org. Chem. 49, 384, (1984)].

Examples of the acylalkylnaphthalene of formula (II) produced in this way include
2-methyl-6-acetylnaphthalene,
2-methyl-6-propionylnaphthalene
2-methyl-6-isobutyrylnaphthalene,
2-methyl-7-acetylnaphthalene,
2-methyl-7-propionylnaphthalene,
2-methyl-7-isobutyrylnaphthalene
2-ethyl-6-acetylnaphthalene,
2-ethyl-6-propionylnaphthalene,
2-ethyl-6-isobutyrylnaphthalene,
2-methyl-6-pivaloylnaphthalene,
2-ethyl-6-pivaloylnaphthalene,
2-ethyl-7-acetylnaphthalene,
2-ethyl-7-propionylnaphthalene,
2-ethyl-7-isobutyrylnaphthalene,
2-methyl-7-pivaloylnaphthalene,
2-ethyl-7-pivaloylnaphthalene,
2-isopropyl-6-acetylnaphthalene,
2-isopropyl-6-propionylnaphthalene,
2-isopropyl-6-isobutyrylnaphthalene,
2-isopropyl-7-acetylnaphthalene,
2-isopropyl-7-propionylnaphthalene,
2-isopropyl-7-isobutyrylnaphthalene,
1-methyl-6-acetylnaphthalene,
1-methyl-6-propionylnaphthalene,
1-methyl-6-isobutyrylnaphthalene,
1-methyl-7-acetylnaphthalene,
1-methyl-7-propionylnaphthalene, and
1-methyl-7-isobutyrylnaphthalene.

Of these acylalkylnaphthalene, compounds of the following formula

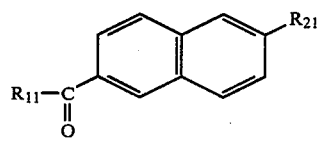 (II-1)

wherein $R_{11}$ represents a lower alkyl group, and $R_{21}$ represents an alkyl group having 1 to 3 carbon atoms, are especially interesting from an industrial viewpoint. Above all, 2-methyl-6-acetylnaphthalene, 2-ethyl-6-acetylnaphthalene, 2-methyl-6-propionylnaphthalene, 2-methyl-6-isobutyrylnaphthalene and 2-methyl-6-pivaloylnaphthalene are preferred.

By the oxidation of the acylalkylnaphthalene of formula (II) with the peroxide in accordance with step (a), the acyloxyalkylnaphthalene of formula (III) is formed in good yields. The product can be precipitated as crystals by cooling the reaction mixture. As required, the resulting crystals may be washed with the same reaction medium as used in the above reaction.

Specific examples of the acyloxyalkylnaphthalene of formula (III) include
2-methyl-6-acetyloxynaphthalene,
2-methyl-6-propionyloxynaphthalene,
2-methyl-6-isobutyryloxynaphthalene,
2-methyl-6-pivaloyloxynaphthalene,
2-methyl-7-acetyloxynaphthalene,
2-methyl-7-propionyloxynaphthalene,
2-methyl-7-isobutyryloxynaphthalene,
2-methyl-7-pivaloyloxynaphthalene,
2-ethyl-6-acetyloxynaphthalene,
2-ethyl-6-propionyloxynaphthalene,
2-ethyl-6-isobutyryloxynaphthalene,
2-ethyl-6-pivaloyloxynaphthalene,
2-ethyl-7-acetyloxynaphthalene,
2-ethyl-7-propionyloxynaphthalene,
2-ethyl-7-isobutyryloxynaphthalene,
2-ethyl-7-pivaloyloxynaphthalene,
2-isopropyl-6-acetyloxynaphthalene,
2-isopropyl-6-propyloxynaphthalene,
2-isopropyl-6-isobutyryloxynaphthalene,
2-isopropyl-7-acetyloxynaphthalene,
2-isopropyl-7-propionyloxynaphthalene,
2-isopropyl-7-isobutyryloxynaphthalene,
1-methyl-6-acetyloxynaphthalene,
1-methyl-6-propionyloxynaphthalene, 1-methyl-6-isobutyryloxynaphthalene,
1-methyl-7-acetyloxynaphthalene,
1-methyl-7-propionyloxynaphthalene, and
1-methyl-7-isobutyryloxynaphthalene.

The acyloxyalkylnaphthalene is subjected to the oxidation of the next step (b). In particular, the acyloxyalkylnaphthalene crystals of formula (III) obtained by oxidizing the acylalkylnaphthalene of formula (II) with the peroxide in a specific formic acid/water reaction medium in accordance with the preferred embodiment have a high purity, and without a recrystallization treatment to be described, can be submitted to step (b).

It has been found in accordance with this invention on the other hand that when the acyloxyalkylnaphthalene crystals of formula (III) obtained in step (a) are recrystallized from acetic anhydride prior to being subjected to step (b), the efficiency of the oxidation reaction in step (b) is markedly increased, and the conversion of the starting acyloxyalkylnaphthalene reaches almost 100% whereas it is normally about 60 mole %.

The suitable amount of acetic anhydride used in the recrystallization procedure is generally at least 3 parts by weight, preferably 5 to 10 parts by weight, per part by weight of the acyloxyalkylnaphthalene crystals. The heating temperature is one sufficient to dissolve the crystals completely, and temperatures in the range of 35° to 140° C. are usually convenient. The heating can be carried out under pressure, but industrially it is sufficient to carry it out under normal atmospheric pressure.

The heating time is one sufficient for the acyloxyalkylnaphthalene crystals to dissolve uniformly in acetic anhydride, and after the heating, the solution is cooled. The cooling may be carried out by using water or ice. To increase the yield of the crystals, cooling with ice is desirable.

The resulting crystals may be rinsed with acetic anhydride. The amount of acetic anhydride used for the rinsing may be one sufficient to remove the mother liquor from the crystals.

Step (b)

The acyloxyalkylnaphthalene of formula (III) obtained step (a) is oxidized with molecular oxygen in this step to convert it to the corresponding acyloxynaphthoic acid of formula (I).

Generally, this oxidation reaction is carried out in a reaction medium composed of an organic carboxylic acid having 2 to 4 carbon atoms such as acetic acid and propionic acid or a mixture of such a carboxylic acid with acetic anhydride.

The amount of the reaction medium is not critical, and can be varied over a wide range depending upon the type of the starting acyloxyalkylnaphthalene or the reaction conditions used. Usually, it can be used in an amount of at least 2 parts by weight, preferably 3 to 100 parts by weight, per part by weight of the starting acyloxyalkylnaphthalene.

Desirably, the reaction medium contains the least possible water. The inclusion of water in an amount of up to 5% by weight, preferably not more than 1% by weight, based on the total amount of the reaction medium is permissible.

When the carboxylic acid/acetic anhydride mixture is used, the suitable amount of acetic anhydride is generally not more than 100 moles, preferably not more than 30 moles, per mole of the starting acyloxyalkylnaphthalene.

An oxidation catalyst advantageously used in this step is a two-component catalyst composed basically of a bromine compound and a cobalt compound, or a three-component composed basically of these two components and a manganese compound. Examples of the bromine compound are cobalt bromide, hydrobromic acid, manganese bromide and ammonium bromide. Cobalt bromide simultaneously plays a role of the cobalt compound, and manganese bromide simultaneously plays a role of the manganese compound. Organic acid salts such as cobalt acetate, cobalt propionate and cobalt naphthenate, and inorganic acid salts such as cobalt nitrate and cobalt carbonate and cobalt complexes such as cobalt acetylacetonate may be cited as examples of the cobalt compound other than cobalt bromide. The amounts of the bromine compound and the cobalt compound are not critical. Conveniently, the amount of the bromine compound is generally at least 100 ppm by weight, preferably 200 to 10,000 ppm by weight, more preferably 200 to 5000 ppm by weight, as Br, and the amount of the cobalt compound is at least 10 ppm by weight, preferably 50 to 5000 ppm by weight, more preferably 100 to 5000 ppm by weight, as Co. Examples of the manganese compound include organic acid salts such as manganese acetate and manganese propionate, inorganic acid salts such as manganese nitrate, and manganese complex salts such as manganese acetylacetonate in addition to manganese bromide. The amount of the manganese compound is generally at least 5000 ppm by weight, preferably 50 to 5000 ppm by weight, more preferably 100 to 5000 ppm by weight, as Mn.

The reaction temperature is generally 100° to 200° C., preferably 110° to 150° C. The reaction pressure is atmospheric pressure to 200 kg/cm$^2$-G, preferably 2 to 60 kg/cm$^2$-G.

Molecular oxygen used as an oxidizing agent can be fed to the reaction system as a pure oxygen gas. Usually, however, an oxygen-containing gas diluted with an inert gas, such as air, is preferably used. It is generally sufficient that the partial pressure of oxygen is not more than 40 kg/cm$^2$. The oxidation reaction proceeds even under a partial pressure of oxygen less than 0.2 kg/cm$^2$, but usually pressures in the range of 0.4 to 12 kg/cm$^2$ are convenient.

The oxidation reaction can be carried out usually by feeding predetermined amounts of the starting compound, the reaction medium and the catalyst into a pressure vessel equipped with a stirrer, heating the mixture to a predetermined temperature, and passing air or an oxygen-containing gas diluted with an inert gas.

According to the process of this invention described hereinabove, the acyloxynaphthoic acids can be produced in high selectivities and yields without the formation of by-product isomers, and the process is very advantageous industrially.

The acyloxynaphthoic acids obtained by the process of this invention, either as such or as hydroxynaphthoic acid by hydrolyzing the acyloxy group, are used as materials for synthetic resins or synthetic fibers. The acyloxynaphthoic acids obtained by the process of this invention, such as 6-acetyloxy-2-naphthoic acid, have recently attracted attention as a material for polyester fibers having high tenacity or liquid crystal polymers. The present invention can industrially provide such naphthoic acids and is of great commercial significance.

The following Examples illustrate the present invention further. All parts in these examples are by weight.

EXAMPLE 1

A reactor equipped with a stirrer, a reflux condenser and a dropping funnel was charged with 60 parts of ethyl acetate and 29.2 parts of 2-methyl-6-acetylnaphthalene. With stirring, the mixture was heated to 50° C. A mixture composed of 40 parts of formic acid and 6.60 parts of 90% hydrogen peroxide was added dropwise through the dropping funnel. Since the generation of heat was observed during the addition, the rate of addition was adjusted, and as required, the reactor was cooled to maintain the temperature of the inside of the reactor at 50° C. After the addition, the mixture was maintained at the same temperature for 2 hours to terminate the reaction. After the reaction, the contents were cooled to form 2-methyl-6-acetyloxyalkylnaphthalene as crystals. The crystals were rinsed with ethyl acetate, and dried at 60° C. under reduced pressure. Then, 30 parts of crystals of 2-methyl-6-acetyloxyalkylnaphthalene were mixed with 240 parts of acetic anhydride. The mixture was heated at 95° C., and cooled. The crystals were separated by filtration and used as a starting material for the following oxidation.

A 200 cc titanium pressure vessel equipped with a stirrer was charged with 10 parts of 2-methyl-6-acetyloxynaphthalene, 80 parts of acetic acid, 20 parts of acetic anhydride, 0.249 parts (Co=590 wt. ppm) of cobalt acetate tetrahydrate, 0.245 parts (Mn=550 wt. ppm) of manganese acetate tetrahydrate, and 0.250 parts (Br=2040 wt. ppm) of ammonium bromide. The vessel was pressurized with air to 25 kg/cm$^2$-G, and the mixture was heated to 120° C. Air was introduced into the vessel at a rate of 10 Nl/hr. When the absorption of oxygen ceased, the reaction was terminated. The reaction time was 2.5 hours. The vessel was cooled, and the contents were withdrawn and analyzed. The conversion of 2-methyl-6-acetyloxynaphthalene was 100 mole %, and the yield of 6-acetyloxy-2-naphthoic acid was 68.5 mole % (selectivity 68.5 mole %). At this time, 23.5 mole % of 6-acetyloxy-2-naphthaldehyde was also formed.

EXAMPLE 2

The 2-methyl-6-acetyloxynaphthalene obtained in the first half of Example 1 was not recrystallized from acetic anhydride prior to oxidation, but was directly oxidized with molecular oxygen in the presence of the same catalyst as in Example 1 in the same reactor as in Example 1. The reaction time was 2.4 hours. After the reaction, the product was analyzed. The conversion of 2-methyl-6-acetyloxynaphthalene was 55.5 mole %, and the yield of 6-acetyloxy-2-naphthoic acid was 40.0 mole % (selectivity 72 mole %). At this time, 8.88 mole % of 6-acetyloxy-2-naphthaldehyde was formed.

EXAMPLE 3

In the same reactor as used in Example 1, 40 parts of formic acid and 27.2 parts of 2-methyl-6-isobutyrylnaphthalene was heated to 50° C., and then a mixture of 32.2 parts of formic acid and 5.36 parts of 90% hydrogen peroxide was added dropwise. Since the generation of heat was observed during the addition, the reaction was terminated by the same procedure as in Example 1. The reaction product was treated in the same way as in Example 1 to obtain 2-methyl-6-isobutyryloxynaphthalene as crystals.

Thirty parts of the 2-methyl-6-butyryloxynaphthalene crystals were mixed with 180 parts of acetic anhydride. The mixture was heated to 140° C., and cooled. The crystals were separated by filtration, and used as a starting material for the following oxidation.

The same reactor as used in the second half of Example 1 was charged with 30 parts of the 2-methyl-6-isobutyryloxynaphthalene, 80 parts of acetic acid, 20 parts of acetic anhydride, 1.87 parts (Co=4425 wt. ppm), of cobalt acetate tetrahydrate, and 1.08 parts (Br=8813 wt. ppm) of ammonium bromide, and pressurized to 10 kg/cm$^2$-G. The mixture was heated to 150° C., and air was introduced into the reactor at a rate of 10 Nl/hr. The reaction was terminated when the absorption of oxygen ceased. The reaction time was 2.4 hours. The reaction mixture was cooled, and the contents were withdrawn and analyzed. The conversion of 2-methyl-6-isobutyryloxynaphthalene was 100 mole %, and 65.0 mole % (selectivity 65.0 mole %) of 6-isobutyryloxy-2-naphthoic acid. At this time, 21.0 mole % of 6-isobutyryloxy-2-naphthaldehyde formed.

EXAMPLE 4

Crystals of 2-methyl-7-propionyloxynaphthalene (34.2 parts) and 273.6 parts of acetic anhydride were mixed, and heated to 95° C. The mixture was then cooled, and the crystals were separated by filtration.

The same reactor as used in the second half of Example 1 was charged with 11.4 parts of the resulting 2-methyl-7-propionyloxynaphthalene crystals, 90 parts of acetic acid, 10 parts of acetic anhydride, 0.249 part (Co=5990 we. ppm) of cobalt acetate tetrahydrate, 0.245 part (Mn=550 wt. ppm) of manganese acetate tetrahydrate, and 0.250 part (Br=2040 wt. ppm) of ammonium bromide, and pressurized to 8 kg/cm$^2$-G. The mixture was heated to 180° C., and air was introduced into the reactor at a rate of 10 Nl/hr. The reaction was terminated when the absorption of oxygen ceased. The reaction time was 2 hours. The reactor was cooled, and the contents were withdrawn and analyzed. The conversion of 2-methyl-7-propionyloxynaphthalene was 100 mole %, and the yield of 7-propionyloxy-2-naphthoic acid was 51.0 mole % (selectivity 51 mole %). At this time, 19 mole % of 7-propionyloxy-2-naphthaldehyde was formed.

EXAMPLE 5

A reactor equipped with a stirrer, a reflux condenser and a dropping funnel was charged with 12.4 g of water, 40 g of formic acid and 29.2 g of 2-methyl-6-acetylnaphthalene, and with stirring, the mixture was maintained at 29° C. on a water bath.

Then, 49.8 g of a mixture prepared in advance from 30.12 g of formic acid, 10.04 g of water and 9.64 g of 90% hydrogen peroxide was added drowpise to the mixture through the dropping funnel over the course of 3 minutes with stirring (formic acid concentration 74.7 wt. %).

The generation of heat was observed during the addition. As required, the reactor was cooled with water and the temperature of the mixture was maintained at 29° C. After the addition, the mixture was reacted at 29° C. for about 5 hours.

After the reaction, crystals of 2-methyl-6-acetyloxynaphthalene were separated from the reaction mixture, rinsed with an aqueous solution of formic acid, and dried at 60° C. under reduced pressure. The product was analyzed by gas-chromatography. It was found that the conversion of 2-methyl-6-acetylnaphthalene was 94.4 mole %, and the selectivity of 6-acetyloxynaphthalene was 93.4 mole %.

A 500 ml titanium autoclave equipped with a stirrer was charged with 5.5 g of 2-methyl-6-acetyloxynaphthalene, 100 g of acetic acid having a water content of 0.2% by weight, 10 g of acetic anhydride, 1.16 g (Co=2500 wt. ppm) of cobalt acetate tetrahydrate, 1.23 g (Mn=2500 wt. ppm) of manganese acetate tetrahydrate and 0.384 g (Br=2850 wt. ppm) of ammonium bromide, and pressurized with air to 2.3 to 3.0 kg/cm$^2$. The mixture was heated to 117° to 123° C.

Air was introduced into the reactor at a rate of 30 Nl/hr, and the reaction was continued until the absorption of oxygen ceased. The reaction time was 1 hour.

The contents were taken out, and analyzed by high-performance liquid chromatography. It was found that the conversion of 2-methyl-6-acetyloxynaphthalene was 97.2 mole % and the yield of 6-acetyloxy-2-naphthoic acid was 88.8 mole % (selectivity 91.3 mole %).

EXAMPLE 6

Water (1.14 g), 11.46 g of formic acid and 8.58 g of 2-methyl-6-acetylnaphthalene were added to a reaction vessel equipped with a stirrer, a reflux condenser and a dropping funnel, and maintained at 20° C. on a water bath. Then, 12.64 g of a mixture prepared in advance from 10 g of formic acid and 2.64 g of 90% hydrogen peroxide was added dropwise through the dropping funnel with stirring over the course of 82 minutes (formic acid concentration 93.9% by weight).

The generation of heat was observed during the addition. As required, the reaction vessel was cooled with water, and the temperature of the mixture was maintained at 17° to 23° C. After the addition, the mixture was reacted at 17° to 23° C. for about 5 hours. The reaction product was analyzed in the same way as in Example 5. The conversion of 2-methyl-6-acetylnaphthalene was 89.1 mole %, and the selectivity of 2-methyl-6-acetyloxynaphthalene was 100 mole %.

A 500 ml titanium autoclave equipped with a stirrer was charged with 5.5 g of the 2-methyl-6-acetyloxynaphthalene, 100 g of acetic acid (water content 0.2% by weight), 10 g of acetic anhydride, 0.047 g (Co=100 wt. ppm) of cobalt acetate tetrahydrate, 0.442 g (Mn=900 wt. ppm) of manganese acetate tetrahydrate, and 0.384 g (Br=2850 wt. ppm) of ammonium bromide, and pressurized with air to 1.7 to 2.2 kg/cm$^2$-G. The reactor was heated to 118° to 124° C.

Air was introduced at a rate of 27 Nl/hr, and the reaction was continued until the absorption of oxygen ceased. The reaction time was 1 hour.

The contents were withdrawn, and analyzed by high-performance liquid chromatography. It was found that the conversion of 2-methyl-6-acetyloxynaphthalene was 96.2 mole %, and the yield of 6-acetyloxy-2-naphthoic acid was 80.3 mole % (selectivity 83.4 mole %).

EXAMPLE 7

A reaction vessel equipped with a stirrer, a reflux condenser and a dropping funnel was charged with 14.64 g of water, 22.28 g of formic acid and 7.86 g of 2-methyl-6-acetylnaphthalene, and with stirring the mixture was maintained at 40° C. over a water bath.

Then, 14.77 g of a mixture prepared in advance from 5 g of water, 7.31 g of formic acid and 2.46 g of 90% hydrogen peroxide was added dropwise to the mixture through the dropping funnel over 30 minutes with stirring. The concentration of formic acid was 59.8% by weight.

The generation of heat was observed during the addition. As required, the reaction vessel was cooled with water to maintain the temperature of the mixture at 40° C. After the addition, the mixture was reacted at 40° C. for about 5 hours. Crystals of 2-methyl-6-acetyloxynaphthalene were separated from the reaction mixture, rinsed with an aqueous solution of formic acid, and dried at 60° C. under reduced pressure. The reaction product was analyzed, and it was found that the conversion of 2-methyl-6-acetylnaphtalene was 81.1 mole %, and the selectivity of 2-methyl-6-acetyloxynaphthalene was 92.7 mole %.

A 500 ml. titanium autoclave equipped with a stirrer was charged with 5.5 g of the resulting 2-methyl-6-acetyloxynaphthalene, 100 g of acetic acid (water content 0.2% by weight), 10 g of acetic anhydride, 0.349 g (Co=750 wt. ppm) of cobalt acetate tetrahydrate, 0.123 g (Mn=250 wt. ppm) of manganese acetate tetrahydrate, and 0.384 g (Br=2850 wt. ppm) of ammonium bromide, and pressurized with air to 1.7-2.1 kg/cm$^2$-G. Then, the mixture was heated to 118° to 123° C. Air was introduced into the autoclave at a rate of 40 Nl/hr, and the reaction was continued until the absorption of oxygen ceased. The reaction time was 1 hour. The contents were taken out, and analyzed by high-performance liquid chromatography. It was found that the conversion of 2-methyl-6-acetyloxynaphthalene was 100 mole %, and the yield of 6-acetyloxy-2-naphthoic acid was 86.0 mole % (selectivity 86.0 mole %). The selectivity of 6-hydroxy-2-naphthoic acid was 0.5 mole %.

EXAMPLE 8

A reaction vessel equipped with a stirrer, a reflux condenser and a dropping funnel was charged with 5.04 g of ethyl acetate and 7.39 g of 2-methyl-6-acetylnaphthalene, and with stirring the mixture was maintained at 30° C. over a water bath.

Then, 7.8 g of a mixture prepared in advance from 5.03 g of formic acid, 0.5 g of water and 2.27 g of 90% hydrogen peroxide was added dropwise to the mixture through the dropping funnel over 19 minutes with stirring. The concentration of formic acid was 46.6% by weight.

The generation of heat was observed during the addition. As required, the reaction vessel was cooled with water to maintain the temperature of the mixture at 30° C. After the addition, the mixture was reacted at 30° C. for about 10 hours. Crystals of 2-methyl-6-acetyloxynaphthalene were separated from the reaction mixture, rinsed with an aqueous solution of formic acid, and dried at 60° C. under reduced pressure. The reaction product was analyzed as in Example 5, and it was found that the conversion of 2-methyl-6-acetylnaphthalene was 95.8 mole %, and the selectivity of 2-methyl-6-acetyloxynaphthalene was 92.7 mole %.

A 500 ml. titanium autoclave equipped with a stirrer was charged with 5.5 g of the resulting 2-methyl-6-acetyloxynaphthalene, 100 g of acetic acid (water content 0.2% by weight), 10 g of acetic anhydride, 0.244 g (Co=525 wt. ppm) of cobalt acetate tetrahydrate, 0.244 g (Mn=500 wt. ppm) of manganese acetate tetrahydrate, and 0.384 g Br=2850 wt. ppm) of ammonium bromide, and pressurized with air to 2 kg/cm$^2$-G. Then, the mixture was heated to 115° to 116° C. Air was introduced into the autoclave at a rate of 71 Nl/hr, and the reaction was continued until the absorption of oxygen ceased. The reaction time was 2 hours. The contents were taken out, and analyzed by high-performance liquid chromatography. It was found that the conversion of 2-methyl-6-acetyloxynaphthalene was 100 mole %, and the yield of 6-acetyloxy-2-naphthoic acid was 88.2 mole % (selectivity 88.2 mole %).

EXAMPLE 9

A reactor equipped with a reflux condenser and a dropping funnel was charged with 47.6 g of water, 163.1 g of formic acid and 12.53 g of 2-methyl-6-acetylnaphthalene, and the mixture was maintained at 26° to 27° C. over a water bath.

The charged mixture was withdrawn from the reactor by means of an external circulating pump, and while recycling it to the reactor via a condenser at a rate of 10 Nl/min., a mixture prepared in advance from 24.9 g of formic acid, 9.29 g of water and 3.86 g of 90% hydrogen peroxide was added dropwise over 12 minutes through the dropping funnel.

After the addition, the reaction was continued at 28° to 30° C. for 6 hours while circulating the reaction mixture at a rate of 10 Nl/min. After the reaction, the desired product was separated from the reaction mixture. A gas-chromatographic analysis of the product showed that the conversion of 2-methyl-6-acetylnaphthalene was 88.2 mole %, and the selectivity of 2-methyl-6-acetyloxynaphthalene was 99.6 mole %.

The resulting 2-methyl-6-acetyloxynaphthalene was oxidized in the same way as in Example 5 under the conditions shown in Table 1. The results are shown in Table 1.

EXAMPLE 10

A reaction vessel equipped with a stirrer, a reflux condenser and a dropping funnel was charged with 6.22 g of water, 21.32 g of formic acid and 3.14 g of 2-methyl-6-acetylnaphthalene, and with stirring, the mixture was maintained at 29° C. over a water bath. Then, 14.48 g of a mixture prepared in advance from 10.03 g of formic acid, 3.45 g of water and 1.0 g of 90% hydrogen peroxide was added through the dropping funnel over 14 minutes with stirring (the formic acid concentration was 76.2% by weight). The generation of heat was observed during the addition. As required, the reaction vessel was cooled with water to maintain the temperature of the mixture at 30° C. After the addition, the mixture was reacted at 30° C. for about 6 hours. After the reaction, the desired product was separated from the reaction mixture. A gas-chromatographic analysis of the product showed that the conversion of 2-methyl-6-acetylnaphthalene was 91.4 mole %, and the selectivity of 2-methyl-6-acetyloxynaphthalene was 91.5 mole %.

The resulting 2-methyl-6-acetyloxynaphthalene was oxidized in the same way as in Example 5 under the conditions shown in Table 1. The results are shown in Table 1.

EXAMPLE 11

A reaction vessel equipped with a stirrer, a reflux condenser and a dropping funnel was charged with 2.5 g of formic acid and 7.3 g of 2-methyl-6-acetylnaphthalene, and with stirring, the mixture was maintained at 30° C. over a water bath. Then, 6.23 g of a mixture prepared in advance from 2.5 g of formic acid, 1.41 g of water and 2.32 g of 90% hydrogen peroxide was added through the dropping funnel over about 60 minutes with stirring (the formic acid concentration was 75.3% by weight). The generation of heat was observed during the addition. As required, the reaction vessel was cooled with water to maintain the temperature of the mixture at 30°-31° C. After the addition, the mixture was maintained at 30° C. for about 60 minutes. The temperature was raised to 35° C., and the mixture was reacted for 1 hour. Further, the temperature of the mixture was raised to 40° C., and the mixture was reacted for 1 hour. Then, the mixture was reacted at 50° C. for 30 minutes.

Finally, the mixture was reacted at 55° C. for 30 minutes.

After the reaction, the desired product was separated from the reaction mixture. A gas-chromatographic analysis of the product showed that the conversion of 2-methyl-6-acetylnaphthalene was 87.5 mole %, and the selectivity of 2-methyl-6-acetyloxynaphthalene was 91.8 mole %.

The resulting 2-methyl-6-acetyloxynaphthalene was oxidized in the same way as in Example 5 under the conditions shown in Table 1. The results are shown in Table 1.

EXAMPLES 12-14

2-Methyl-6-acetyloxynaphthalene obtained under the same reaction conditions as in the first step reaction in Example 5 was oxidized in the same way as in Example 5 under the conditions shown in Table 1. The results are shown in Table 1.

In Example 12, the concentration of water in the reaction medium before the start of oxidation with air was about 0.2% by weight.

In Example 13, the air oxidation reaction was carried out in a glass reactor.

TABLE 1

| Example | 9 | 10 | 11 | 12 | 13 | 14 |
|---|---|---|---|---|---|---|
| Feed | | | | | | |
| 2-Methyl-6-acetyloxynaphthalene (g) | 5.5 | 22.4 | 4 | 5.5 | 4 | 10 |
| Acetic acid (g) | 100 | 142.6 | 312.7 | 109.2 | 65.3 | 62 |
| Acetic anhydride (g) | 10 | 40.7 | 7.3 | 0.8 | 14.7 | 18 |
| Cobalt acetate tetrahydrate (g) | 0.244 | 0.407 | 0.71 | 0.244 | 0.177 | 0.178 |
| Manganese acetate tetrahydrate (g) | 0.244 | 0.407 | 0.71 | 0.244 | 0.177 | 0.178 |
| Ammonium bromide (g) | 0.038 | 0.814 | 1.117 | 0.384 | 0.279 | 0.356 |
| Reaction conditions | | | | | | |
| Co (wt. ppm) | 525 | 525 | 525 | 525 | 525 | 525 |
| Mn (wt. ppm) | 500 | 500 | 500 | 500 | 500 | 500 |
| Br (wt. ppm) | 280 | 3620 | 2850 | 2850 | 2850 | 3630 |
| Reaction temperature (°C.) | 117-124 | 115 | 116 | 117-121 | 110-117 | 110 |
| Reaction pressure (kg/cm$^2$-G) | 1.9-2.0 | 25 | 25 | 2.1-2.2 | 0 | 50-61 |
| Conversion of 2-methyl-6-acetyloxynaphthalene (mole %) | 100 | 100 | 91.8 | 92.2 | 97.4 | 100 |
| Selectivity of 6-acetyloxy-2-naphthoic acid (mole %) | 83.1 | 75.4 | 87.9 | 92 | 82.2 | 87 |
| Selectivity of 6-hydroxy-2-naphthoic acid (mole %) | trace | 0.8 | 1.0 | 5.5 | 1.2 | 0 |

TABLE 1-continued

| Example | 9 | 10 | 11 | 12 | 13 | 14 |
|---|---|---|---|---|---|---|
| Yield of 6-acetyloxy-2-naphthoic acid (mole %) | 83.1 | 75.4 | 80.7 | 84.8 | 80.0 | 87 |

EXAMPLE 15

A reaction vessel equipped with a stirrer, a reflux condenser and a dropping funnel was charged with 3.1 g of water, 10 g of formic acid and 12.1 g of 2-methyl-6isobutyrylnaphthalene, and with stirring the mixture was maintained at 29° C. over a water bath.

Then, 12.45 g of a mixture prepared in advance from 7.53 g of formic acid, 2.51 g of water and 2.41 g of 90% hydrogen peroxide was added dropwise to the mixture through the dropping funnel over 3 minutes with stirring. The concentration of formic acid was 74.7% by weight.

The generation of heat was observed during the addition. As required, the reaction vessel was cooled with water to maintain the temperature of the mixture at 29° C. After the addition, the mixture was reacted at 29° C. for about 5 hours. Crystals of 2-methyl-6-isobutyryloxynaphthalene were separated from the reaction mixture, rinsed with an aqueous solution of formic acid, and dried at 60° C. under reduced pressure. The reaction product was analyzed, and it was found that the conversion of 2-methyl-6-isobutyrylnaphthalene was 97 mole %, and the selectivity of 2-methyl-6-isobutyryloxynaphthalene was 75 mole %.

A 500 ml. titanium autoclave equipped with a stirrer was charged with 10 g of the resulting 2-methyl-6-isobutyryloxynaphthalene, 100 g of acetic acid (water content 0.2% by weight), 10 g of acetic anhydride, 0.244 g (Co=525 wt. ppm) of cobalt acetate tetrahydrate, 0.244 g (Mn=500 wt. ppm) of manganese acetate tetrahydrate, and 0.384 g (Br=2850 wt. ppm) of ammonium bromide, and pressurized with air to 25 kg/cm$^2$-G. Then, the mixture was heated to 120° C. Air was introduced into the autoclave at a rate of 25 Nl/hr, and the reaction was continued until the absorption of oxygen ceased. The reaction time was 2.5 hours. The contents were taken out, and analyzed by high-performance liquid chromatography It was found that the conversion of 2-methyl-6-isobutyryloxynaphthalene was 100 mole %, and the yield of 6-isobutyryloxy-2-naphthoic acid was 78.5 mole % (selectivity 78.5 mole %).

EXAMPLE 16

A reaction vessel equipped with a stirrer, a reflux condenser and a dropping funnel was charged with 3.1 g of water, 10 g of formic acid and 10.6 g of 2-ethyl-6acetylnaphthalene, and with stirring the mixture was maintained at 29° C. over a water bath.

Then, 12.45 g of a mixture prepared in advance from 7.53 g of formic acid, 2.51 g of water and 2.41 g of 90% hydrogen peroxide was added dropwise to the mixture through the dropping funnel over 3 minutes with stirring. The concentration of formic acid was 74.7% by weight.

The generation of heat was observed during the addition. As required, the reaction vessel was cooled with water to maintain the temperature of the mixture at 29° C. After the addition, the mixture was reacted at 29° C. for about 5 hours. Crystals of 2-ethyl-6-acetyloxynaphthalene were separated from the reaction mixture, rinsed with an aqueous solution of formic acid, and dried at 60° C. under reduced pressure. The reaction product was analyzed, and it was found that the conversion of 2-ethyl-6-acetylnaphthalene was 94 mole %, and the selectivity of 2-ethyl-6-acetyloxynaphthalene was 90 mole %.

A 500 ml. titanium autoclave equipped with a stirrer was charged with 10 g of the resulting 2-ethyl-6-acetyloxynaphthalene, 100 g of acetic acid (water content 0.2% by weight), 10 g of acetic anhydride, 0.244 g (Co=525 wt. ppm) of cobalt acetate tetrahydrate, 0.244 g (Mn=500 wt. ppm) of manganese acetate tetrahydrate, and 0.384 g (Br=2850 wt. ppm) of ammonium bromide, and pressurized with air to 25 kg/cm$^2$-G. Then, the mixture was heated to 120° C. Air was introduced into the autoclave at a rate of 25 Nl/hr, and the reaction was continued until the absorption of oxygen ceased. The reaction time was 2.5 hours. The contents were taken out, and analyzed by high-performance liquid chromatography. It was found that the conversion of 2-ethyl-6-acetyloxynaphthalene was 100 mole %, and the yield of 6-acetyloxy-2-naphthoic acid was 76.3 mole % (selectivity 76.3 mole %).

EXAMPLE 17

A reaction vessel equipped with a stirrer, a reflux condenser and a dropping funnel was charged with 10 g of glacial acetic acid and 5 g of 2-methyl-6-acetylnaphthalene, and with stirring the mixture was heated to 50° C. over a water bath. Then, 9.4 g of a mixture prepared in advance from 21 g of glacial acetic acid and 3.5 g of 90% hydrogen peroxide was added dropwise through the dropping funnel over about 5 minutes with stirring. Vigorous generation of heat was observed during the addition. As required, the reaction vessel was cooled with water to maintain the temperature of the mixture at 50° C. After the addition, the reaction was continued at the same temperature for 60 minutes, and then the desired product was separated. A gas-chromatographic analysis of the product showed that the conversion of 2-methyl-6-acetylnaphthalene was 45 mole %, and the selectivity of 2-methyl-6-acetyloxynaphthalene was 82 mole %.

The reaction mixture was cooled, and the resulting crystals were washed with ethyl acetate and dried at 60° C. under reduced pressure to obtain 2-methyl-6-acetyloxynaphthalene. Thereafter, 30 parts of the 2-methyl-6-acetyloxyalkylnaphthalene crystals were mixed with 240 parts of acetic anhydride. The mixture was heated at 95° C., and cooled. The crystals were collected by filtration and used as a starting material in the following oxidation reaction.

A 30 cc four-necked glass flask equipped with a reflux condenser, a material feed opening, a reaction solution withdrawing opening and an oxygen feed opening was charged with 1.5 g of the resulting 2-methyl-6-acetyloxynaphthalene, 27.3 g of acetic acid, 2.7 g of acetic anhydride, 0.063 g (Co=500 wt. ppm) of cobalt acetate tetrahydrate, 0.067 g (Mn=500 wt. ppm) of manganese acetate tetrahydrate and 0.1 g (Br=2720 wt. ppm) of ammonium bromide, and the mixture was heated at 111° to 114° C. over an oil bath.

Oxygen was introduced into the flask under atmospheric pressure at a rate of 3.8 Nl/hr through a glass ball filter. After confirming that oxidation began, a solution prepared in advance from 1.5 parts of 2-methyl-6-acetyloxynaphthalene, 30 parts of acetic acid, 0.063 part (Co=500 wt. ppm) of cobalt acetate tetrahydrate, 0.067 part (Mn=500 wt. ppm) of manganese acetate tetrahydrate, 0.102 part (Br=2690 wt. ppm) of bromoacetyl bromide ($BrCH_2COBr$) and water in an amount to provide a water concentation of 1.99% by weight was fed at a rate of 29 g/hr. The reaction solution was withdrawn from the flask while the liquid surface level of the reactor was maintained constant. In about 4 hours after the start of the reaction, the reaction became steady. The product was analyzed by high-peformance liquid chromatography. It was found that the conversion of 2-methyl-6-acetyloxynaphthalene was 86.9 mole %, the selectivity of 6-acetyloxy-2-naphthoic acid was 55 mole %, the selectivity of

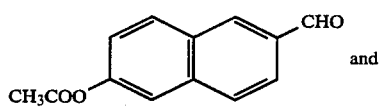

and

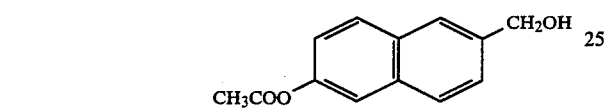

as intermediates was 39 mole % in total, and the selectivity of 6-hydroxy-2-naphthoic acid was 1.1 mole %.

The water concentration of the reaction solution withdrawn when the reaction became steady was 2.4% by weight.

EXAMPLE 18

A reaction vessel equipped with a stirrer, a reflux condenser and a dropping funnel was charged with 10 g of benzene and 6 g of 2-methyl-6-acetylnaphthalene. Then, 9.4 g of a mixture prepared in advance from 21 g of formic acid and 3.5 g of 90% hydrogen peroxide was added dropwise over about 5 minutes through the dropping funnel with stirring at 60° C. After the addition, the mixture was maintained at the same temperature for about 60 minutes. After the reaction, the product was analyzed by gas-chromatography. The conversion of 2-methyl-6-acetylnaphthalene was 40 mole %, and the selectivity of 2-methyl-6-acetyloxynaphthalene was 60 mole %.

The reaction solution was cooled, and the resulting crystals were rinsed with ethyl acetate and dried at 60° C. under reduced pressure to give 2-methyl-6-acetyloxynaphthalene. Then, prior to oxidation, 30 parts of the 2-methyl-6-acetyloxynaphthalene were mixed with 240 parts of acetic anhydride, and the mixture was heated at 95° C. It was then cooled, and the crystals were separated by filtration and used in the following oxidation reaction.

A 300 ml titanium autoclave equipped with a stirrer was used and the same oxidation reaction as in Example 17 was carried out.

A solution prepared in advance from 1.5 g of 2-methylacetyloxynaphthalene, 27.3 g of acetic acid, 2.7 g of acetic anhydride, 0.063 g of cobalt acetate tetrahydrate, 0.067 g of manganese acetate tetrahydrate and 0.1 g of ammonium bromide was fed in an amount of 94.9 g, and heated to 120° C. Air was passed under a pressure of 25 kg/cm²-G. After confirming that oxidation began, the same starting solution as in Example 17 and having a water concentration of 5% by weight was fed at a rate of 175 g/hr. The reaction was continued at 120° to 125° C. After the reaction became steady, the product was analyzed by high-performance liquid chromatography. It was found that the conversion of 2-methyl-6-acetyloxynaphthalene was 98.3 mole %, the selectively of 6-acetyloxy-2-naphthhoboic acid was 83.7 mole %, the selectivity of the same aldehyde and alcohol intermedaites as in Example 17 was 6.1 mole % in total, and the selectivity of 6-hydroxy-2-naphthoic acid was 2.3 mole %.

We claim:

1. A process for producing an acyloxynaphthoic acid represented by the general formula

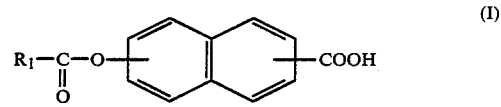 (I)

wherein $R_1$ represents a hydrogen atom or an alkyl group having 1 to 10 carbon atoms,

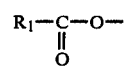

is bonded to the 6- or 7-position of naphthalene ring which comprises (a) oxidizing an acylalkylnaphthalene represented by the general formula

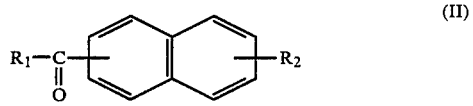 (II)

wherein $R_1$ is as defined above, and $R_2$ represents a lower alkyl group having 1 to 3 carbon atoms, $R_2$ is bonded to the 2-position of naphthalene ring, and

is bonded to the same position as defined above, with a peroxide, and recrystallizing the resulting acyloxyalkylnaphthalene represented by the general formula

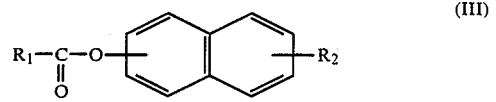 (III)

wherein $R_1$ and $R_2$ are as defined above, with acetic anhydride, and then (b) oxidizing the acyloxyalkylnaphthalene represented by the above general formula (III) with molecular oxygen in an organic carboxylic acid having 2 to 4 carbon atoms or mixture thereof with acetic anhydride in the presence of a catalyst comprising a bromine compound and cobalt compound.

2. The process of claim 1 wherein the peroxide is hydrogen peroxide.

3. The process of claim 1 wherein the oxidation of the acylalkylnaphthalene of general formula (II) with the peroxide is carried out in a reaction medium composed of an organic solvent selected from the group consisting of lower aliphatic carboxylic acids, aliphatic carboxylic acid esters, aromatic hydrocarbons and mixtures of two or more of these compounds.

4. The process of claim 3 wherein the reaction medium is used in an amount of 1 to 60 parts by weight per part by weight of the acylalkylnaphthalene of general formula(II).

5. The process of claim 3 wherein the organic solvent as reaction medium is selected from the group consisting of formic acid, acetic acid, propionic acid, methylformate, ethylformate, methyl acetate, ethyl acetate, methyl propionate, ethyl propionate, benzene, toluene, xylene, ethylbenzene and mixtures of two or three of these compounds.

6. The process of claim 1 wherein a compound represented by the following formula

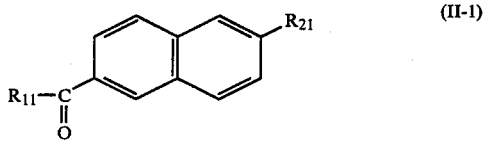

wherein $R_{11}$ represents a lower alkyl group, and $R_{21}$ represents an alkyl group having 1 to 3 carbon atoms, is used as the acylalkylnaphthalene of general formula (11).

7. The process of claim 1 wherein the acylalkylnaphthalene is selected from the group consisting of 2-methyl-6-acetyl-naphthalene, 2-ethyl-6-acetylnaphthalene, 2-methyl-6-propionyl-naphthalene, 2-methyl-6-isobutyrylnaphthalene and 2-methyl-6-pivaloylnaphthalene.

8. The process of claim 1 wherein the oxidation of the acylalkylnaphthalene of general formula (II) with the peroxide is carried out at a temperature of about 0° to about 150° C.

9. The process of claim 1 wherein the peroxide is used in amount of 0.1 to 10 moles per mole of the acylalkylnaphthalene of general formula (II).

10. The process of claim 1 wherein the acetic anhydride for recrystallization is used in an amount of at least 3 parts by weight per by weight of acyloxyalkyl-naphthalene of general formula (III).

11. The process of claim 1 wherein the amount of the bromine compound, calculated Br, is 100 to 10,000 ppm by weight based on the reaction medium.

12. The process of claim 1 wherein the amount of the cobalt compound, calculated as Co, is 10 to 5,000 ppm by weight based on the reaction medium.

13. The process of claim 1 wherein the catalyst further comprises a manganese compound.

14. The process of claim 13 wherein the amount of the manganese compound, calculated as Mn, is not more than 5,000 ppm by weight based on the reaction medium.

15. The process of claim 1 wherein the oxidation of acyloxyalkylnaphthalene of general formula (III) is carried out at a temperature of about 100° to about 200° C. under atmospheric pressure to 200 kg/cm²-G.

16. The process of claim 1 wherein the acetic anhydride used as a reaction medium of oxidation in step (b) is used in an amount of not more than 100 moles of acyloxyalkylnaphthalene of general formula (III).

* * * * *